US00PP09187P

United States Patent [19]

Dehan

[11] Patent Number: Plant 9,187

[45] Date of Patent: Jul. 4, 1995

[54] IMPATIENS PLANT NAMED 'BINGO'

[75] Inventor: Klara Dehan, Holon, Israel

[73] Assignee: Danziger "Dan" Flower Farm, Moshav Mishmar Hashiva, Israel

[21] Appl. No.: 299,614

[22] Filed: Sep. 2, 1994

[51] Int. Cl.[6] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Foley & Lardner

[57] ABSTRACT

A new and distinct cultivar of Impatiens plant named Bingo, characterized by its very large orange-red flowers, compact growth habit, excellent branching, dark green leaves, and its pleasantly contrasting foliage and flower colors.

1 Drawing Sheet

The present invention relates to a new and distinctive cultivar of Impatiens plant, botanically known as Impatiens, commercially known as New Guinea Impatiens, and known by the cultivar name Bingo.

The new cultivar was developed by the inventor Klara Dehan in Mishmar Hashiva, Israel in a controlled breeding program. The female or seed parent was a cultivar identified by the breeding number DC-4532, and the male or pollen parent was a cultivar identified by the breeding number PC-6199. Both parents are proprietary cultivars used in the breeding program. The new cultivar was selected by the inventory from the progeny of the stated cross.

Asexual reproduction of the new cultivar by leaf cuttings performed by the inventory in Mishmar Hashiva, Israel has established that the unique features of this new Impatiens are stabilized and are reproduced true to type in successive propagations.

The following characteristics in combination distinguish the new Impatiens Bingo from both its parent varieties and other cultivated Impatiens of this type known and used in the floriculture industry:

1. Compact growth habit.
2. Excellent branching.
3. Very large flowers, orange-red in color.
4. Dark green foliage, infused with purple.
5. The orange-red flower color and dark green leaves provide a very attractive plant.
6. The plant is particularly suited for hanging baskets.

The accompanying color photographic drawing illustrates the overall appearance of the cultivar, with the colors being as true as it is reasonably possible to obtain in a colored reproduction of this type.

The following is a detailed description of the new Impatiens cultivar based on plants produced under commercial practice in Mishmar Hashiva, Israel. The plants described were grown in a net-covered greenhouse during the summer season with temperatures ranging from 35° C. maximum to 18° C. minimum. Color references are made to the Royal Horticulatural Society Colour chart except where general terms of ordinary dictionary significance are used.

The new cultivar is similar in general orange-red flower color to Antigua, described in U.S. Plant Pat. No. 8,283. However, Bingo is distinguished from Antigua by its much larger diameter flowers, and its more compact growth habit that results in a much shorter pot plant.

Parentage: The female parent DC-4532 and the male parent PC-6199 are seedlings from breeding program.

Propagation:

*Type cutting.*—Leaf cuttings.

*Time to initiate roots.*—7–8 days at 25° C. summer; 7–9 days at 20° C. winter.

*Rooting habit.*—Roots well.

Plant Description:

*Form.*—Excellent self-branching produces a full, rounded symmetrical plant.

*Habit of growth.*—Compact growth habit.

*Foliage.*—Size: Medium; mature leaves 8.0 cm long and 3.5 cm wide. Shape: Lanceolate to ovate. Margin: Serrated. Color: Young foliage, top side 147A infused with purple, and under side 187A; mature foliage, top side 147A infused with purple, and under side 187A. Venation: Purple.

Flowering description:

*Flowering habits.*—The initiation of flower buds takes about 5–6 weeks from potting leaf cutting. Flower completely opens approximately 9–10 weeks after potting.

*Natural flowering season.*—The new cultivar flowers under ambient conditions in Israel all year, but in the winter season with less light, there are fewer flowers.

*Flower buds.*—Buds before opening are approximately 2.0 cm in length and 1.5 cm in width. Length of spur is 4 cm, and length of pedicel is 4.5 cm.

*Flowers borne.*—Flowers are carried on strong stems and are fully open from initiation in about 2 weeks; flowering continues all season.

*Quantity of flowers.*—Very floriferous; 15–20 flowers open at the same time, and flowering is continuous.

*Petals.*—Shape: Two (2) pairs of heart-shaped petals and a single larger petal; petals overlap. Color: Top side when opening is 43A, with no noticeable fading; under side is 43B; Number of petals: Five (5). Size of flowers: Very large, about 8 cm in diameter.

*Reproductive organs.*—Stamens: One (1) in number. Anthers: Round, purple color. Pollen color: White. Pistils: Stigma: Round in shape, nearly white in color. Ovaries: Four (4) in number, 1 mm in size; light green in color.

Disease resistance: No significant disease problem noted to date.

I claim:

1. A new and distinct cultivar of Impatiens plant named Bingo, as illustrated and described.

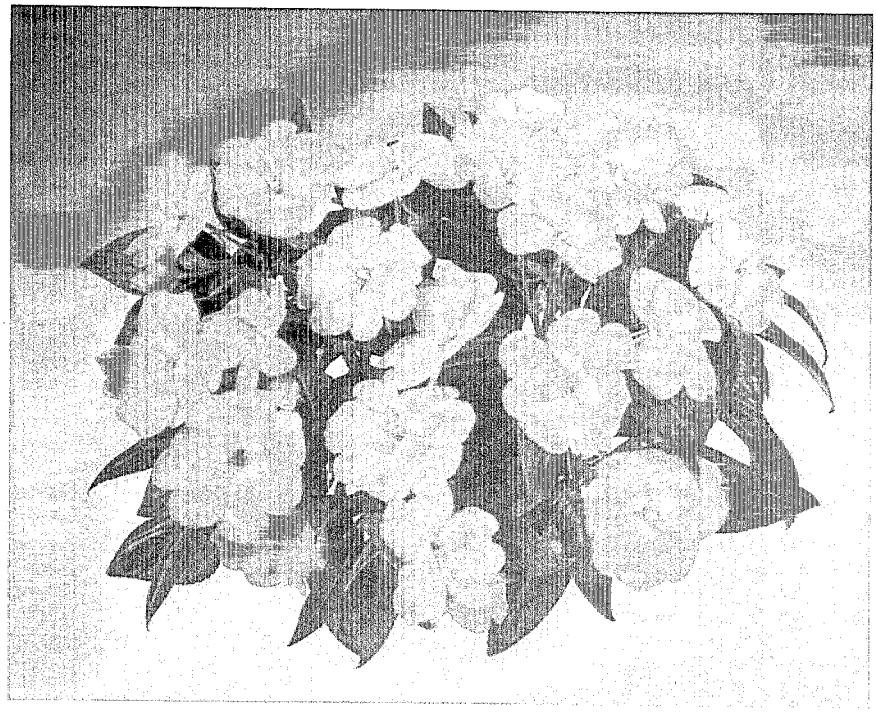

* * * * *